US009554871B2

(12) United States Patent
Kovnatsky et al.

(10) Patent No.: US 9,554,871 B2
(45) Date of Patent: Jan. 31, 2017

(54) 2-WIRE ULTRASONIC MAGNETOSTRICTIVE DRIVER

(71) Applicant: Dentsply International, Inc., York, PA (US)

(72) Inventors: Ilya Kovnatsky, Holland, PA (US); Michael C. Dietrich, East Petersburg, PA (US); Peter H. Werner, Columbia, PA (US); David C. Klunk, New Oxford, PA (US); Kenneth R. Guaragno, Spring Grove, PA (US)

(73) Assignee: Dentsply International, Inc., York, PA (US)

( * ) Notice: Subject to any disclaimer, the term of this patent is extended or adjusted under 35 U.S.C. 154(b) by 33 days.

(21) Appl. No.: 14/743,402

(22) Filed: Jun. 18, 2015

(65) Prior Publication Data

US 2015/0366631 A1    Dec. 24, 2015

Related U.S. Application Data

(60) Provisional application No. 62/013,698, filed on Jun. 18, 2014.

(51) Int. Cl.
*A61C 1/07* (2006.01)
*A61C 1/00* (2006.01)
*A61C 17/20* (2006.01)

(52) U.S. Cl.
CPC .............. *A61C 1/07* (2013.01); *A61C 1/0015* (2013.01); *A61C 17/20* (2013.01)

(58) Field of Classification Search
None
See application file for complete search history.

(56) References Cited

U.S. PATENT DOCUMENTS 4,110,908 A * 9/1978 Cranston ................ A61C 1/07
                                                    310/26
4,445,065 A * 4/1984 Albert .................... G01L 1/162
                                                    310/25

(Continued)

FOREIGN PATENT DOCUMENTS

| WO | WO2006/125066 | * | 5/2006 |
| WO | WO 2008/061225 | | 5/2008 |
| WO | WO 2008/083366 | | 7/2008 |

OTHER PUBLICATIONS

Aviv et al., "Smudge Attacks on Smartphone Touch Screens", WOOT, 2010, 10 pages.

(Continued)

*Primary Examiner* — Brian T Gedeon
(74) *Attorney, Agent, or Firm* — Baker & Hostetler LLP

(57) ABSTRACT

A method for controlling a magnetostrictive ultrasonic transducer of the type used in a magnetostrictive ultrasonic dental scaler includes generating a drive signal for a resonant circuit using a full bridge synchronous class D amplifier. The electrical signal output by the resonant circuit drives an excitation coil that generates an electromagnetic field that causes the magnetostrictive ultrasonic transducer to vibrate. A feedback wire is rendered unnecessary by measuring current and voltage outputs of the resonant circuit and quadrature sampling the measured current and voltage outputs at the same sampling rate as used for the generation of the electrical signal by the resonant circuit. A pulse width modulated signal is generated from the quadrature sampled sensed current and voltage that represents a pulse train approximation of a sine wave of the drive signal for, in turn, being applied to the full bridge synchronous class D amplifier to generate the drive signal for the resonant circuit. Changes in the pulse widths of the pulse train change the amplitude of the drive signal.

34 Claims, 6 Drawing Sheets

(56) References Cited

U.S. PATENT DOCUMENTS

| | | | |
|---|---|---|---|
| 4,992,779 A | 2/1991 | Sugino et al. | |
| 5,395,240 A | 3/1995 | Paschke et al. | |
| 6,190,167 B1* | 2/2001 | Sharp | A61C 17/20 |
| | | | 433/119 |
| 6,241,520 B1 | 6/2001 | Gofman et al. | |
| 6,503,081 B1 | 1/2003 | Feine | |
| 7,533,830 B1 | 5/2009 | Rose | |
| 7,614,878 B2 | 11/2009 | Paschke et al. | |
| 7,715,167 B2 | 5/2010 | Edel et al. | |
| 2003/0222535 A1* | 12/2003 | Gofman | B06B 1/0253 |
| | | | 310/316.01 |
| 2006/0238068 A1 | 10/2006 | May et al. | |
| 2007/0058402 A1 | 3/2007 | Shekhawat et al. | |
| 2007/0249941 A1 | 10/2007 | Salehi et al. | |
| 2011/0087605 A1 | 4/2011 | Pond | |
| 2011/0140815 A1 | 6/2011 | Jamnia | |
| 2011/0241576 A1 | 10/2011 | Paschke | |
| 2011/0250559 A1 | 10/2011 | Feine | |

OTHER PUBLICATIONS

"Controls, Touchscreen Comfortsense 7000, 7 Day Programmable Thermostat: 4 Heat/2 Cool Universal Multi-Stage", Lennox Engineering Data, Bulletin No. 210515, Jun. 2009, 1-8.

"Operation and Maintenance Instruction Manual: ASC-12 Piezoelectric Scaler", Aseptico, Aug. 2009, 1-16.

Shahzad et al., "Secure Unlocking of Mobile Touch Screen Devices by Simple Gestures—You Can See It But You Can Not Do It", Mobicom, Oct. 2013, 1-12.

* cited by examiner

2-WIRE ULTRASONIC MAGNETOSTRICTIVE DRIVER

CROSS-REFERENCE TO RELATED APPLICATIONS

This application claims benefit of Provisional Application No. 62/013,698 filed Jun. 18, 2014. The content of that patent application is hereby incorporated by reference in its entirety.

TECHNICAL FIELD

The invention relates to an ultrasonic magnetostrictive driver and, more particularly, to a magnetostrictive driver that uses a microcontroller, a class D full bridge amplifier, and a current/voltage feedback system to ensure that the magnetostrictive transducer is operating at optimal operational frequency (OOF), voltage, and bias current without requiring a feedback wire in the cable.

BACKGROUND

Ultrasonic dental scalers are generally used to clean patients' teeth and for other ultrasonic procedures such as general supra and sub-gingival scaling applications, periodontal debridement for all types of periodontal diseases, and endodontic procedures, for example. Dental scalers include a control circuit and a handpiece having an ultrasonic transducer, an energizing coil, magnetostrictive stack and a tool tip. In operation, the energizing coil surrounds the magnetostrictive stack and is energized by engaging a foot pedal that engages the control circuit to provide an electric current to the energizing coil. This, in turn, actuates the ultrasonic transducer by activating a stack of plates of magnetostrictive material that expands and contracts when subjected to a time-varying electro-magnetic field generated by the energizing coil in response to the electric current. In particular, the time-varying electro-magnetic field is created by directing a time-varying electric current through the excitation coil surrounding the magnetostrictive stack which causes the tool tip to vibrate at the resonant frequency of the ultrasonic transducer. The vibrating tool tip is then used by the dental practitioner to clean a patient's teeth by, for example, removing plaques and other debris from the surface of the patient's teeth.

Vibration of the tool tip is controlled and adjusted as appropriate during operation to tune the frequency and amplitude of the electric current applied to the transducer to a desired optimal operational frequency and amplitude of the ultrasonic transducer. As operational conditions change, such as load on the tool tip, temperature, density of the material being removed, and the like, the operational frequency and amplitude change accordingly and it becomes necessary to adjust the time-varying electric current to, in turn, adjust the time-varying electro-magnetic field to maintain the desired optimal operational frequency and amplitude. For this purpose, automatic frequency and amplitude tuning circuits have been developed in the prior art that use feedback coils, phase locked loops, and the like, to adjust the frequency and amplitude during operation to the resonant frequency of the natural acoustic modes of vibration of the magnetostrictive stack to optimize the vibration energy applied to the tool tip.

For example, U.S. Pat. No. 6,241,520 discloses an automatically tuned drive circuit for driving an ultrasonic scaling probe at a desired frequency of operation based on the choice of scaler insert for the handpiece. The oscillator of the drive circuit is coupled to the energizing coil in the handpiece for applying an oscillatory current to the magnetostrictive element. The drive circuit includes a frequency detector for sensing the frequency of the magnetostrictive element, and the detector's output signal further designates the magnitude of the frequency. The drive circuit responds to the sensed value of the frequency amplitude and adjusts a current applied to the energizing coil to adjust the oscillation frequency commanded by the scaling probe.

U.S. Pat. No. 7,614,878 similarly discloses a system for dynamically controlling an ultrasonic magnetostrictive dental scaler by providing a control circuit including a digital signal processor that processes sensed feedback signals regarding frequency and amplitude of the vibrations and filters the signals through dynamic filter loops to obtain error and/or control signals to adjust a voltage controlled oscillator that, in turn, controls the amplitude and phase characteristics of the time-varying electric current applied to the energizing coil. Varying the amplitude and phase of the time-varying electric current controls the output of the dental scaler so as to control the frequency and amplitude of the vibrations of the dental scaler to the desired operating point.

U.S. Pat. No. 6,503,081 discloses the use of a microprocessor in the drive circuitry to set the frequency of oscillation such that the power delivered to the excitation coil is maximized. The microprocessor is programmed to sense the power input to the excitation coils and the voltage-current phase difference measurements or power response slope measurements are used to determine the maximum power transfer point in order to set the oscillation frequency to the resonant frequency of the magnetostrictive insert.

U.S. Pat. No. 7,715,167 also discloses a control unit for setting the frequency of the excitation current flowing in an excitation coil of a magnetostrictive ultrasonic dental device. The control unit employs a voltage-controlled oscillator (VCO) that generates a variable frequency signal, a driver for setting up and regulating the excitation current according to the variable frequency signal from the VCO, a current sensor in series with the excitation coil that outputs a current-sense signal corresponding to the current flowing through the excitation coil, a functional block that receives the current-sense signal and outputs a function signal proportional to the sensed current, and a microprocessor that receives the function signal and controls the VCO according to the function signal. This control unit differs from other prior art control units in that even though the feedback which controls the frequency of oscillation is solely in connection with the sensed current passing through the excitation coil, the excitation coil is not part of the VCO circuit and is not directly connected to the VCO circuit.

The excitation coil in the handpiece is electrically connected via a cable to the control unit that provides the excitation energy to the excitation coil. The cable typically includes two input wires connected across the terminals of the excitation coil for driving the excitation coil as well as a third wire that provides the current-sense feedback to the control circuit for use in adjusting the current to the excitation coil to maintain the optimal operational frequency as discussed above. Unfortunately, the third wire adds significant weight to the cable, which increases cable drag that increases strain on the clinician's hand, wrist, and forearm during use. Also, the feedback control loop complicates the circuitry needed to maintain the operation of the ultrasonic transducer at the desired optimal operational frequency for optimal operation, and the circuitry is generally inefficient, generates too much heat during operation, and accordingly, does not permit the device to be as compact as desired.

It is desirable to provide an ultrasonic magnetostrictive driver that does not require the feedback wire and thus may support a lightweight cable and that is small and efficient to ensure that the magnetostrictive transducer is operating at the desired optimal operational frequency without generating excess heat. The invention addresses these and other needs in the art.

SUMMARY

The above and other needs in the art are addressed by providing an ultrasonic magnetostrictive driver that does not require a feedback signal from the handpiece to maintain the magnetostrictive transducer at the desired optimal operational frequency. A two-wire approach is enabled by using a full bridge synchronous class D amplifier and a power control circuit that drives the transducer at its optimal operational frequency without requiring a feedback wire in the cable to implement a closed loop feedback arrangement.

Exemplary embodiments are directed to a magnetostrictive ultrasonic dental scaler and a method for controlling a magnetostrictive ultrasonic transducer of the type used in a magnetostrictive ultrasonic dental scaler. The method includes generating a drive signal for a resonant circuit using a full bridge synchronous class D amplifier. The electrical signal output by the resonant circuit drives an excitation coil that generates an electromagnetic field that causes the magnetostrictive ultrasonic transducer to vibrate. A feedback wire from a feedback loop including the handpiece is rendered unnecessary by measuring current and voltage outputs of the ultrasonic transducer by quadrature sampling the measured current and voltage outputs at the same sampling rate as used for the generation of the electrical signal by the resonant circuit. A pulse width modulated signal is generated from the quadrature sampled sensed current and voltage that represents a pulse train approximation of a sine wave of the drive signal and is applied to the full bridge synchronous class D amplifier to generate the drive signal for the resonant circuit. Changes in the pulse widths of the pulse train change the amplitude of the drive signal.

In exemplary embodiments, the quadrature sampling step includes an oscillator generating a NCO frequency that is a multiple of an optimal operational frequency of the resonant circuit and driving the full bridge synchronous class D amplifier at the NCO frequency. For example, the NCO frequency may be n times the optimal operational frequency of the ultrasonic transducer whereby a cycle of the optimal operational frequency is divided into n samples each having a period of duration T1 corresponding to a 360°/n phase of the optimal operational frequency. The NCO frequency thus synchronizes the rate of the quadrature sampling with the optimal operational frequency of the ultrasonic transducer. Respective values representing pulse durations of the pulse trains are stored in each of the n periods of duration T1 in lookup tables for each side of the full bridge synchronous class D amplifier, and each lookup table stores respective pulses that are 180° out of phase with corresponding pulses sampled during the same sampling period of the other lookup table. Preferably, corresponding pulses in the respective lookup tables are offset by a pulse width value that is adjustable so as to induce a bias current to enable dynamic adjustment of a bias current output by the resonant circuit. The address for the lookup tables is provided by clocking an x bit counter at the NCO frequency, where $2^x=n$, and using a value of the x bit counter as an address for the lookup tables for each T1 period.

In exemplary embodiments, the sampling frequency is generated using a numerically controlled oscillator implemented as an m-bit phase accumulator register that on each clock cycle of the NCO frequency is incremented by a frequency control word (FCW). A current angular position of the numerically controlled oscillator is stored for a phase calculated as phase=$2*\pi*(FCW/2m)$. In an exemplary embodiment, the x bit counter is clocked by a most significant bit of the numerically controlled oscillator.

During operation, the optimal operational frequency of the ultrasonic transducer is determined by measuring an amplitude relationship between current and voltage outputs of the resonant circuit. The quadrature sampling of the amplitude relationship between current and voltage outputs of the resonant circuit is at the same sampling rate as used at an output of the numerically controlled oscillator at specific values of the x-bit counter. In an exemplary embodiment, voltage and current samples are taken 0, 90, 180, and 270 degrees phase shifted from the drive signal of the resonant circuit. From these values, the amplitude relationship between current and voltage outputs of the resonant circuit is calculated as:

$$|V|=0.5*\text{sqrt}((V_0-V_{180})^2+(V_{90}-V_{270})^2)$$

$$|I|=0.5*\text{sqrt}((I_0-I_{180})^2+(I_{90}-I_{270})^2).$$

The impedance (Z) of the ultrasonic transducer is calculated from the amplitude of the voltage and current waveforms as:

$$Z=|V|/|I|,$$

where V is the output voltage of the resonant circuit and I is the input current of the ultrasonic transducer and the optimal operational frequency is selected from a curve of impedance versus frequency. The optimal operational frequency may be determined by exciting the ultrasonic transducer at a variety of frequencies in a frequency range, calculating the impedance Z of the ultrasonic transducer at each of the variety of frequencies, and determining the optimal operational frequency as a frequency in the frequency range at which the impedance has a minimum value on an impedance versus frequency curve.

The method is implemented in any of a number of devices including a magnetostrictive ultrasonic transducer, such as a magnetostrictive ultrasonic dental scaler including a handpiece having an ultrasonic transducer that vibrates at an optimal operational frequency in response to an electromagnetic field applied thereto and an excitation coil that generates the electromagnetic field in response to an applied electrical signal. A resonant circuit controlled by a control circuit generates the electrical signal, and the control circuit implements the magnetostrictive ultrasonic transducer control method. In exemplary embodiments, the control circuit includes a microprocessor and a full bridge synchronous class D amplifier that generates a drive signal for the resonant circuit. In operation, the control circuit receives sensed current and voltage outputs of the ultrasonic transducer as a result of changing impedance at the ultrasonic transducer. The microprocessor quadrature samples the sensed current and voltage outputs at the same sampling rate used for the generation of the electrical signal, generates a pulse width modulated signal from the quadrature sampled sensed current and voltage that represents a pulse train approximation of a sine wave of the drive signal, and the pulse train is applied to the full bridge synchronous class D amplifier to generate the drive signal.

In exemplary embodiments, the resonant circuit includes an LC resonant circuit that when coupled to the ultrasonic transducer produces a high Q resonant circuit in line with a physical resonance of the ultrasonic transducer. A numerically controlled oscillator generates sampling NCO frequency used by the aforementioned method. The NCO frequency is a multiple of an optimal operational frequency of the resonant circuit and is applied to the full bridge synchronous class D amplifier. A cycle of the optimal operational frequency is divided into n samples each having a period of duration T1 corresponding to a 360°/n phase of the optimal operational frequency, and the NCO frequency synchronizes a rate of the quadrature sampling with the optimal operational frequency of the ultrasonic transducer. Lookup tables store respective values representing pulse durations of the pulse trains in each of the n periods of duration T1 for each side of the full bridge synchronous class D amplifier. Each lookup table stores respective pulses that are 180° out of phase with corresponding pulses sampled during the same sampling period of the other lookup table. Preferably, corresponding pulses in the respective lookup tables are offset by a pulse width value that is adjustable so as to induce a bias current to enable dynamic adjustment of a bias current output by the resonant circuit. An x bit counter, where $2^x=n$, is clocked by the numerically controlled oscillator at the NCO frequency, and a value of the x bit counter is used as an address for the lookup tables for each T1 period. The numerically controlled oscillator may be implemented by the microprocessor and include an m-bit phase accumulator register that on each clock cycle of the NCO frequency is incremented by a frequency control word (FCW) whereby a current angular position of the numerically controlled oscillator is stored for a phase calculated as phase=$2*\pi*(FCW/2m)$. A most significant bit of the numerically controlled oscillator may be used to clock the x bit counter. The optimal operational frequency of the ultrasonic transducer may be determined by measuring an amplitude relationship between current and voltage outputs of the resonant circuit, where the amplitude relationship between current and voltage outputs of the resonant circuit is sampled at the same sampling rate as used at an output of the numerically controlled oscillator at specific values of the x-bit counter.

In an exemplary embodiment, the voltage and current samples are taken 0, 90, 180, and 270 degrees phase shifted from the drive signal of the resonant circuit and the microprocessor calculates from the samples the amplitude relationship between current and voltage outputs of the resonant circuit as:

$$|V|=0.5*sqrt((V_0-V_{180})^2+(V_{90}-V_{270})^2)$$

$$|I|=0.5*sqrt((I_0-I_{180})^2+(I_{90}-I_{270})^2).$$

The impedance Z of the ultrasonic transducer may be determined by the microprocessor as $Z=|V|/|I|$, where V is the output voltage of the resonant circuit and I is the input current of the ultrasonic transducer and the optimal operational frequency is a frequency at a central location on a downward slope of impedance Z versus frequency on a curve of impedance Z versus frequency. To find the optimal operational frequency, the microprocessor controls the resonant circuit to generate the electrical signal to excite the ultrasonic transducer at a variety of frequencies in a frequency range, calculates the impedance Z of the ultrasonic transducer at each of the variety of frequencies, and determines the optimal operational frequency as a frequency in the frequency range at which the impedance has a minimum value on an impedance versus frequency curve.

The microprocessor implements the method of the invention to determine the optimal operational frequency of the ultrasonic transducer and to adjust the optimal operational frequency as the impedance at the ultrasonic transducer changes. A Hall effect current sensor may be used to sense an output current of the resonant circuit. Also, the sensed current and voltage outputs of the ultrasonic transducer need not be calculated from the output of the resonant circuit but may be provided via a feedback wire from a feedback loop including the excitation coil.

In exemplary embodiments of a dental scaler, the dental scaler includes a display screen including a touch panel display that controls power applied to the ultrasonic transducer so as to change the output amplitude of the ultrasonic transducer in response to touch panel inputs to the touch panel display. In such an embodiment, an asynchronous data line transmits and receives data between the display and the microprocessor whereby when an event is changed on the display information relating to the change is transmitted on the asynchronous data line to the microprocessor, which interprets the display information and changes the power applied to the ultrasonic transducer and transmits update information back to the display to update a status of the display. In another embodiment, a potentiometer controls power and individual switches control functions whereby changes to the potentiometer and/or individual switches provide a direct analog signal into the microprocessor and the microprocessor interprets any changes in the analog signal to accordingly control power applied to the ultrasonic transducer. The control circuit also may be responsive to a dental chair control panel including a potentiometer or a touch display that provide desired changes in the power applied to the ultrasonic transducer to the microprocessor which controls power applied to the ultrasonic transducer.

BRIEF DESCRIPTION OF THE DRAWINGS

Exemplary embodiments of the invention will be described in conjunction with the associated figures, of which.

DETAILED DESCRIPTION OF ILLUSTRATIVE EMBODIMENTS

Figure 1:
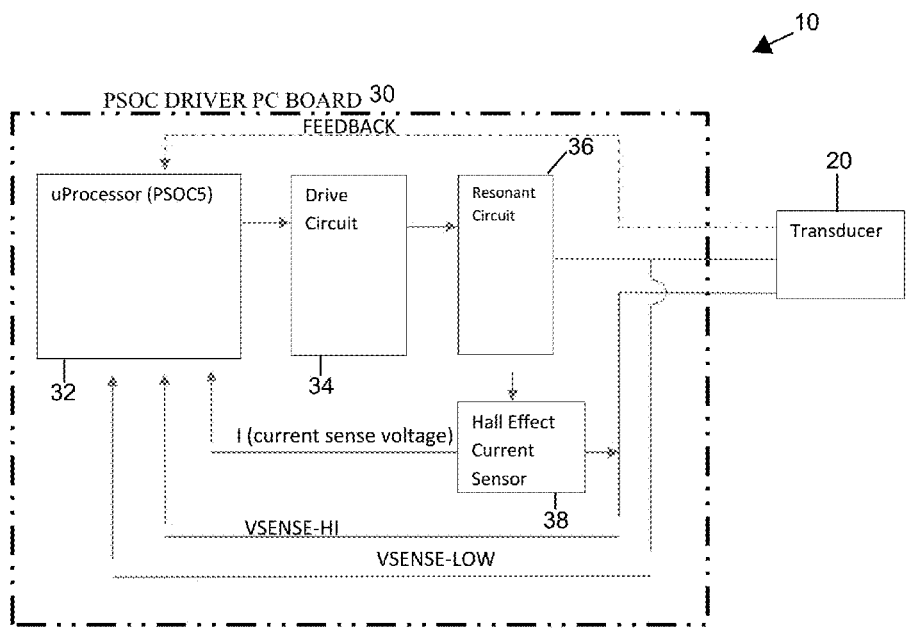
FIG. 1 illustrates a simplified block diagram of a magnetostrictive ultrasonic driver in accordance with the invention.

Certain specific details are set forth in the following description with respect to FIGS. 1-10 to provide a thorough understanding of various embodiments of the invention. Certain well-known details are not set forth in the following disclosure, however, to avoid unnecessarily obscuring the various embodiments of the invention. Those of ordinary skill in the relevant art will understand that they can practice other embodiments of the invention without one or more of the details described below. Also, while various methods are described with reference to steps and sequences in the following disclosure, the description is intended to provide a clear implementation of embodiments of the invention, and the steps and sequences of steps should not be taken as required to practice the invention.

Those skilled in the art will appreciate that embodiments of the invention described herein relate to methods and apparatus for controlling the excitation frequency of current flowing through the excitation coil in which a magnetostrictive transducer element has been placed. In the embodiments described below, a dental scaler apparatus is described as a non-limiting example of an application of the control method and apparatus of the invention. The embodiments described herein are understood to be for illustrative purposes only and not to limit the scope of the invention, which encompasses other dental and comparable medical uses of ultrasonic devices. The term "magnetostrictive ultrasonic device" as used herein is intended to denote any ultrasonic apparatus intended for dental or medical use and which utilizes a magnetostrictive ultrasonic transducer. These and other embodiments of the invention will become apparent from the following detailed description.

The invention relates to a magnetostrictive ultrasonic device that drives an ultrasonic transducer without requiring a closed loop arrangement with a feedback wire and that uses a full bridge class D amplifier for efficient control of either 3-wire or 2-wire ultrasonic systems. As will be explained in more detail below, an exemplary embodiment of the control system is built on the Cypress PSOC technology (Programmable System on Chip) that allows for added utility and functional improvement without the need to change the printed circuit board or to add hardware. The PSOC technology can be both programmed with new software and configured so that its internal hardware elements are utilized when needed.

The ultrasonic system and transducer can be controlled by a number of methods in accordance with the invention. These methods are specific to the type of system the ultrasonic module is installed in. When paired with a display screen in a table top scaler, the ultrasonic module is controlled by a touch panel display of the table top scaler. As the power is changed on the touch panel display, the output amplitude of the transducer follows the change. This is accomplished through an asynchronous (ASIC) data line which transmits and receives data between the FPGA on the display board and the microprocessor of the control circuit (described below). When an event is changed on the display (i.e., power, purge, rinse, etc.), the FPGA on the display board interprets the change. This information is then transmitted on the ASIC line to the microprocessor, which interprets the information and changes the modules status (changing power, opening water solenoid, etc.). Information is then transmitted back to the display to update the display status.

The module also can be installed in a table top unit with a potentiometer controlling power and individual switches controlling functions. In this case, the control is a direct analog signal into the microprocessor of the control circuit. In this case, the microprocessor directly interprets the status change and controls the output to the ultrasonic transducer or solenoid valves.

In another scenario, the ultrasonic module is connected into the dental chair control panel. The dental chair can control power in two ways. The first utilizes the potentiometer to control the output power energizing the ultrasonic transducer. In the second method, the dental chair has its own proprietary display that provides a digital output to the ultrasonic module. The microprocessor of the control circuit interprets the 0-5 V signal to control the output to the ultrasonic transducer. The ultrasonic traducer follows the changes that occur on the dental chair display.

FIG. 1 illustrates a simplified block diagram of a magnetostrictive ultrasonic driver for controlling an ultrasonic transducer in accordance with the invention. As illustrated, the system 10 includes a handpiece 20 having an ultrasonic transducer, an energizing coil, and a tool tip (not shown) for implementing a dental scaler in an exemplary embodiment. The magnetostrictive ultrasonic driver is implemented on a PSOC driver PC board 30 and includes a microcontroller 32 (FIGS. 4-6), drive circuit 34 (FIG. 3), resonant circuit 36, and Hall effect current sensor 38 that provides a current sense voltage to microcontroller 32. As illustrated, the output voltage is measured directly at the output of the resonant circuit 36 and provided as further input to microcontroller 32 for determining the adjustments to the drive circuit for adjusting the output of the resonant circuit 36 to provide the appropriate optimal operational frequency signal across the energizing coil of the handpiece 20 for operating the transducers in the handpiece 20 at the optimal operational frequency (OOF). No secondary coil or sensing coil is required at the handpiece 20, although the drive electronics described below may be used with or without a feedback circuit.

Microcontroller 32 is implemented in an exemplary embodiment by a PSOC5 microcontroller 32 that is used to provide overall control of the system including drive frequency generation, drive circuit control and control of the user interface. As explained in more detail below, microcontroller 32 includes a built-in analog-to-digital converter (ADC), numerically controlled oscillator (NCO) (FIGS. 4-6), and programmable logic (FIGS. 9-10) that together provide integral drive electronics that support the overall system functionality.

Figure 2A:
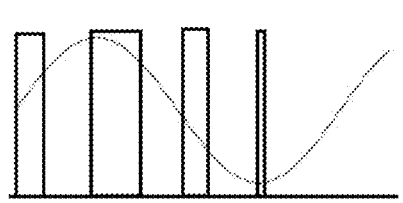
FIGS. 2(a) and 2(b) illustrate pulse width modulated signals used to approximate a sine wave of the drive signal whereby changing the pulse widths changes the amplitude of the drive signal.
Figure 2B:
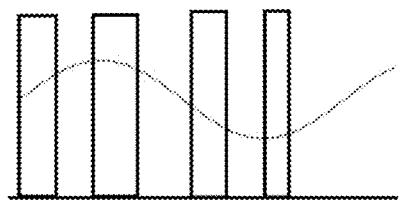
Figure 3A:
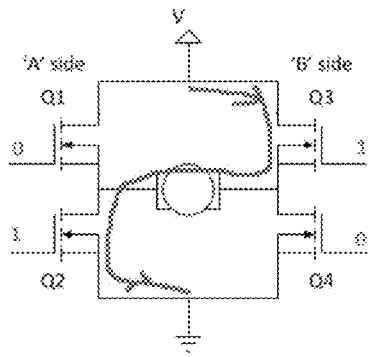
FIGS. 3a and 3b illustrate the operation of a full bridge class D amplifier circuit to dynamically adjust the bias current.
Figure 3B:
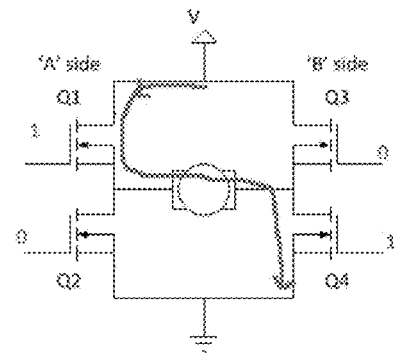

The drive electronics 34 includes a full bridge synchronous class D amplifier including four FETs Q1-Q4 as illustrated in FIG. 3. A full bridge synchronous class D amplifier arrangement allows for optimal efficiency because, unlike traditional analog drive circuits using a linear amplifier, the class D amplifier operates at a frequency greater than the output frequency. In an exemplary embodiment, a 4× frequency is used but higher frequencies can be used. Generally, a sampling frequency may be used that is n times the optimal operating frequency whereby a cycle of the optimal operating frequency is divided into n samples each having a duration corresponding to a 360°/n phase of the optimal operating frequency. Unlike a half bridge amplifier in which one side is connected to ground, the full bridge amplifier includes two half bridges with independent controls for reducing power and capacitor requirements of the drive electronics 34. In operation, the full bridge synchronous class D amplifier generates an output sine wave by generating a pulse width modulated signal having a frequency of 4× the desired output frequency and stores the pulse width modulated signal features for each 90° phase in a lookup table. For example, as can be seen from FIGS. 2(*a*) and 2(*b*), the sine wave is approximated by using the respective pulse trains shown. FIGS. 2(*a*) and 2(*b*) illustrate pulse width modulated signals used to approximate a sine wave of the drive signal whereby changing the pulse widths change the amplitude of the drive signal. By appropriately changing the pulse widths of the drive signal, the amplitude of the output sine can be changed in a manner well-known to those skilled in the art.

The pulse widths for the required sine wave drive signal are stored in lookup tables of microcontroller 32. In an exemplary embodiment, two such tables (TABLE A and TABLE B) are used as described below with respect to FIG. 5. Each table is responsible for one leg of the full bridge synchronous class D amplifier circuit as shown in FIG. 3. FIG. 3 illustrates the operation of the full bridge class D amplifier circuit to dynamically adjust the bias current. In the embodiment of FIG. 3, FETs Q1 and Q2 constitute the 'A' side of the bridge while FETs Q3 and Q4 constitute the 'B' side of the bridge. Table A contains values of the pulse length that enable the 'A' side of the bridge (how long Q1 is on and Q2 is off), while Table B similarly controls the 'B' side (how long Q3 is on and Q4 is off). The two tables A and B are 180 degrees out of phase (i.e., when Table A has the highest on time, Table B has the shortest on time) which, in turn, causes one side of the bridge to drive high (connect to V) while the other side drives low (path to ground) as illustrated in FIG. 3 for different values of Tables A and B. By adding a slight offset (slightly larger pulse width) between the two tables to vary the on/off times of the FETs, a software configurable DC bias current may be generated to provide unused energy back into the power supply without the need of additional electronics, thereby simplifying the drive circuitry and reducing the amount of heat generated. Moreover, by adjusting the offset between the two tables, the bias current can be adjusted dynamically. Also, in FIG. 3, the some current flows back into the power supply and is reused on the next cycle and is not dissipated in a resistive component to generate heat. In operation, the full bridge synchronous class D amplifier circuit adjusts for any back EMF generated by the acoustic transducer that is fed back to the full bridge synchronous class D amplifier circuit via the FETS Q1-Q4, which allows for both drive frequency, amplitude and bias current generation. Using a higher switching frequency (4× the output frequency) also reduces generated EMI.

In exemplary embodiments, each half of the full bridge is implemented using a TPS28225D FET driver IC, which takes a low current switching signal from the microcontroller 32 and produces the necessary high drive currents to quickly switch the gates of 2 FETS (Q1/Q2 or Q3/Q4) in opposite directions. The high current drive of the FET driver IC (not shown) ensures fast switching times and minimal loss in the FETS. Additionally, 2 inline resistors (not shown) may be added to the gate drive to allow for adjusting the rise times of the gate voltage for noise reduction and EMI minimization. The output of each half bridge contains a snubber circuit (not shown) used to minimize high frequency switching noise in the rest of the system (C14, R4).

The output of the full bridge synchronous class D amplifier circuit of the drive circuit 34 is coupled to an LC resonant circuit (L1, L2, C2) 36 of conventional design, which when coupled to the acoustic transducer in the handpiece 20, produces a high Q resonant circuit that is in line with the physical resonance of the acoustic transducer. As known by those skilled in the art, the LC resonant circuit 36 effectively filters out the higher harmonics of the output of the full bridge synchronous class D amplifier leaving only the desired fundamental frequency at the transducer.

Figure 4:
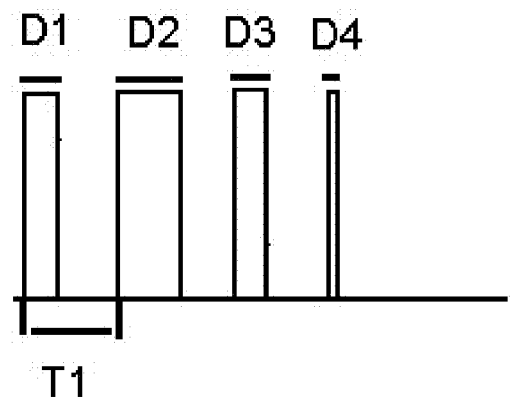
FIG. 4 illustrates different pulse train widths generated from the values in lookup tables and used to control a Numerically Controlled Oscillator (NCO) to generate a frequency (1/T1) which is, for example, 4 times the optimal operational frequency (OOF).

As noted above with respect to FIGS. 2 and 3, lookup tables are used to control and generate the width of the respective pulses of the pulse train. FIG. 4 illustrates different pulse train widths generated from the values in the lookup tables. The NCO 50 functions to change the frequency of a digitally controlled frequency source. As shown in FIG. 4, the values in the lookup tables may be used to establish the pulse widths (D1, D2, D3, D4) for duration T at frequency 1/T. A separate Numerically Controlled Oscillator (NCO) 50 is implemented within the microcontroller 32 to generate the frequency (1/T1), which is, for example, 4× the optimal operational frequency (OOF). An exemplary implementation is a 4× oversampling design in which a cycle is divided up into 4 samples each having a duration of T1. Therefore, the lookup tables (A and B) contain 4 values representing the pulse duration (D1,D2,D3,D4) of a sine wave in each of the four 1/T1 periods. The 2-bit counter 52 thus counts the steps of the phase counter in increments of 0°, 90°, 180°, and 270°. The table values then determine the length of the pulse width in that phase as shown in FIGS. 2(*a*) and 2(*b*).

Figure 5:
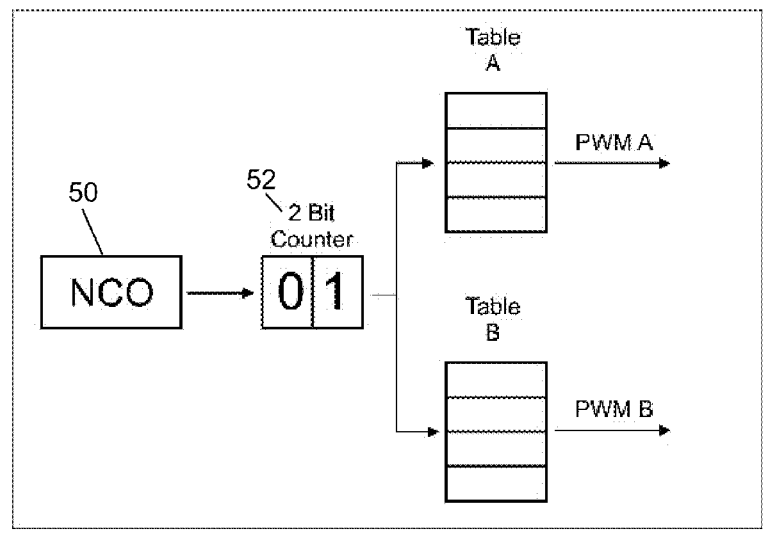
FIG. 5 illustrates a 2 bit counter that is clocked by the NCO to generate values for use as the address in the lookup table for each 1/T1 period whereby the output frequency of the system is the NCO frequency divided by 4.
Figure 6:
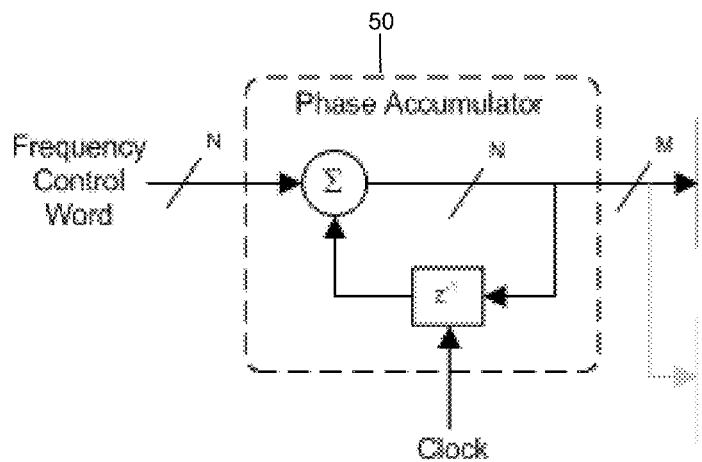
FIG. 6 illustrates a sample n-bit phase accumulator register that on each system clock cycle is incremented by a frequency control word (FCW) to store the current angular position of the NCO from which the phase can be calculated.

FIG. 5 illustrates a 2 bit counter 52 that is clocked by the NCO 50 to generate values for use as the address in the lookup table for each 1/T1 period whereby the output frequency of the system is the NCO frequency divided by 4. It is noted that 2 bit counter 52 is used where n=4 samples per cycle. More generally, the counter is an x bit counter, where $2^x$=n. In an exemplary embodiment, the implementation of the NCO 50 in FIG. 5 includes a 24 bit phase accumulator register (n=24). FIG. 6 illustrates a sample n-bit phase accumulator register (e.g., n=24) that on each system clock cycle is incremented by a frequency control word (FCW) to store the current angular position of the NCO 50 from which the phase can be calculated. The phase accumulator effectively stores the current angular position of the NCO 50, and its phase can be calculated as follows:

$$\text{phase} = 2*\pi*(FCW/2n).$$

By dynamically changing the FCW, one can change how fast the phase accumulator "accumulates." For example, if one sets the FCW to 0x400000, it will take 4 clock cycles for the phase accumulator to cycle $2\pi$. On the other hand, if the FCW is set to 0x1, it will take $2^{24}$ clocks to cycle the same $2\pi$. In the exemplary implementation, only the most significant bit of the NCO 50 (M=1) is used to clock the counter that in turn feeds the lookup tables to determine when to sample the voltage and current values in response to the changing output of the 2-bit counter 52 indicating that a new quadrant of the sine wave has been entered. In this manner, the sampling is at the same sampling rate as used for the signal generation and stays in lockstep with the generated output frequency without requiring zero-crossing detectors for the VCO as in the prior art. Those skilled in the art will appreciate that providing sampling that is synchronous to signal generation allows for a slower sampling rate but maintains the ability to measure phase difference. The technique described herein also measures phase without the use of zero crossing detection and is more accurate than zero crossing detection.

As noted in the background section above, prior art magnetostrictive driver designs generally required secondary sense coils to measure the operational parameters of the transducer. In other implementations, the actual energizing coil is used as the feedback mechanism. The drive circuit of the invention may be used with or without use of such feedback mechanisms, as will be explained more fully below.

In order to maintain the OOF and optimal phase and bias in accordance with the invention without the use of a secondary coil, both the high and low voltages (differentially across the transducer as VSENSE-HI and VSENSE-LOW as shown in FIG. 1) and the current (using the Hall Effect current sensor 38) are measured at the outputs of the resonant circuit 36. In order to determine the OOF, the amplitude relationship between the current and the voltage must be measured. Since the drive frequency of the system is synchronous to the NCO 50, rather than measuring the phase relationship between the voltage and the current directly, they can be individually measured with respect to the NCO 50. For example, the current and the voltage are sampled at the same sampling rate as output by the NCO 50 at specific values of the 2 bit counter (FIG. 5). This process can occur at full speed (the NCO frequency) or subsampled to minimize the processing required.

Figure 7:
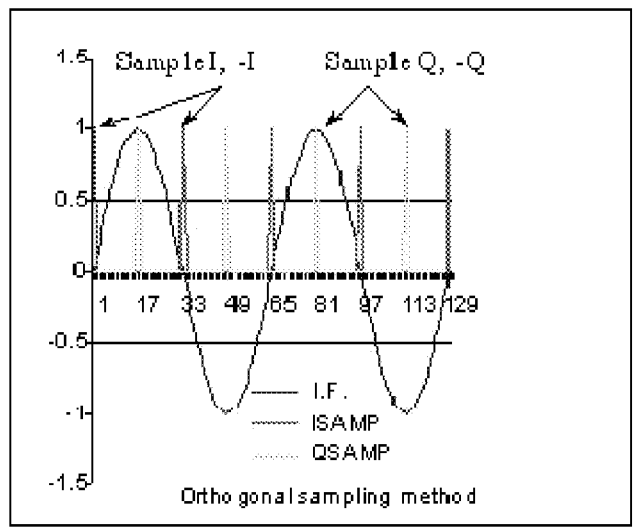
FIG. 7 illustrates Quadrature Orthogonal Sampling as implemented in an exemplary embodiment of the invention.

The voltage and current relationships are measured in exemplary embodiments using quadrature sampling. FIG. 7 illustrates Quadrature Orthogonal Sampling of the NCO 50 as implemented in an exemplary embodiment of the invention where the signal is sampled at precise intervals using heterodyning techniques. As shown in FIG. 7, signals captured at counter values of 0 and 2 are denoted as in-phase (I, −I) samples, while samples captured during counter values of 1 and 3 are denoted as quadrature samples (Q, −Q). This technique is commonly referred to as Quadrature Orthogonal Sampling. In an exemplary embodiment, voltage and current samples are taken 0, 90, 180, and 270 degrees phase shifted from the drive frequency of the resonant circuit 36. From these values, the amplitude relationship between current and voltage outputs of the resonant circuit 36 is calculated as:

$$|V|=0.5*\text{sqrt}((V_0-V_{180})^2+(V_{90}-V_{270})^2)$$

$$|I|=0.5*\text{sqrt}((I_0-I_{180})^2+(I_{90}-I_{270})^2).$$

Figure 8:
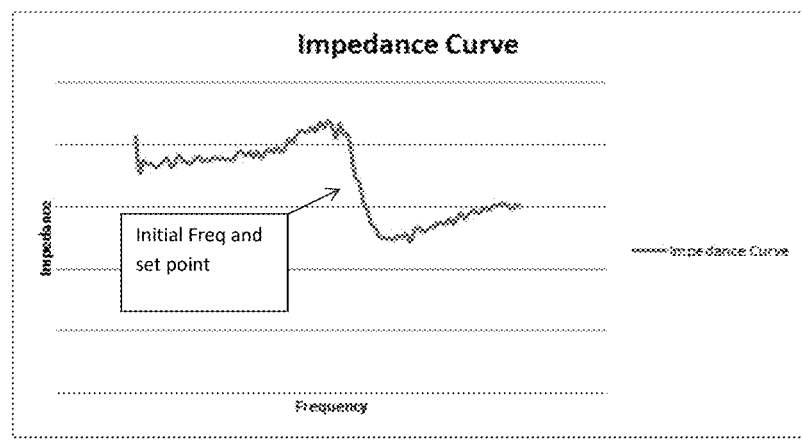
FIG. 8 illustrates an impedance curve versus frequency showing a central location on the downward slope of the impedance curve that is used for the operating point of the transducer in order to ensure a monotonic feedback error signal.

The impedance (Z) of the resonant circuit 36 is calculated from the amplitude of the voltage and current waveforms as:

$$Z=|V|/|I|,$$

where V is the output voltage of the resonant circuit and I is the input current of the transducer and the optimal operational frequency is selected from a curve of impedance versus frequency (FIG. 8). The optimal operational frequency may be determined by exciting the ultrasonic transducer at a variety of frequencies in a frequency range, calculating the impedance Z of the ultrasonic transducer at each of the variety of frequencies, and determining the optimal operational frequency as a frequency in the frequency range at which the impedance has a minimum value on the impedance versus frequency curve.

It has been determined experimentally that the magnitude of the impedance can be used to both determine and to lock onto the OOF. Due to variability of the OOF of typical acoustic transducers, and due to the fact that the feedback signal is not monotonic, it is necessary for the feedback loop to first locate the appropriate operational point. This is accomplished by exciting the transducer to sweep the transducer across a predetermined frequency range at a preset power level while measuring the transducer parameters to identify the resonance frequency of the transducer for changing impedance due to varied loads. This can be done quickly enough (200 ms) without the user noticing any anomalous behavior. This scan can be performed each time that the transducer is activated by the user as described below with respect to FIG. 9. Once the scan is performed, the collected impedance data is filtered. The data is then curve fitted to a piecewise linear function using an iterative approach. This determines the initial frequency and the operating point of the feedback loop. As can be seen from FIG. 8, a central location on the downward inflection slope of the impedance curve (versus frequency) is used for the operating (resonant frequency) point of the transducer in order to ensure a monotonic feedback error signal. Thus, the system can be designed to lock onto the OOF at the central location on the downward slope of the impedance curve for most efficient operation (i.e., where less power is required to maintain the operating voltage applied to the transducer due to resonance).

Once the OOF is measured in this fashion, the system can optionally maintain and adjust the OOF dynamically to maintain frequency lock as described below with respect to FIG. 10. Though in practice it was determined that dynamic adjustment of the OOF was unnecessary since the temperature and the load typically do not change too much, experiments demonstrated that if required a simple Proportional Integrated Derivative (PID) loop was adequate to maintain frequency lock.

Figure 9:
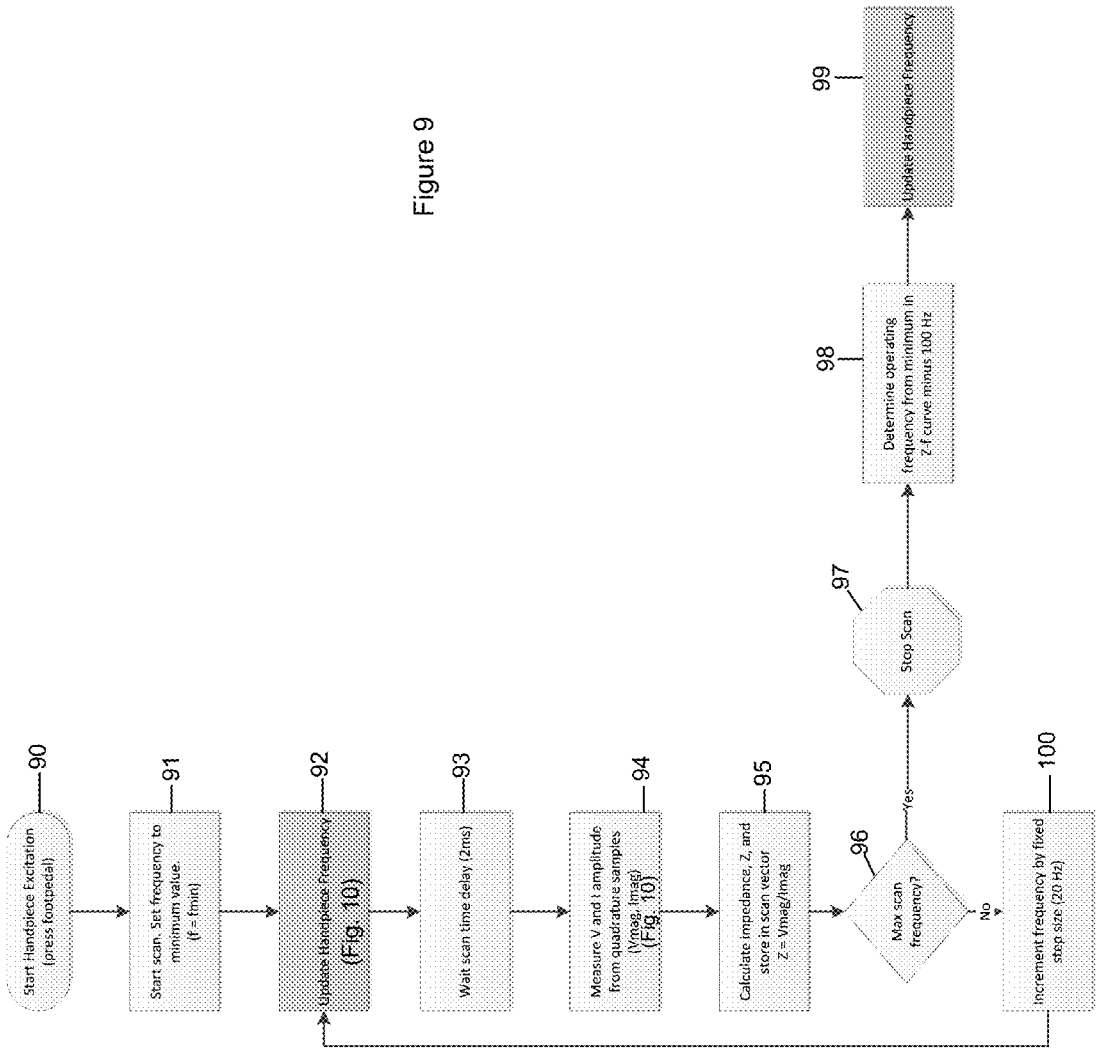
FIG. 9 illustrates sample operation of an ultrasonic handpiece in accordance with an exemplary embodiment of the invention.

FIG. 9 illustrates sample operation of an ultrasonic handpiece in accordance with an exemplary embodiment of the invention. As shown in FIG. 9, excitation of the handpiece 20 is initiated at step 90 by, for example, depressing the foot pedal (not shown) used to activate the drive circuit 34. Then, the operational point is acquired by starting a scan at step 91. The frequency is set to the minimum value ($f=f_{min}$) and the handpiece frequency is updated at step 92 (as elaborated below with respect to FIG. 10). The system waits for an appropriate scan time delay at step 93 (e.g., 2 ms) and then measures the V amplitude (Vmag) and I amplitude (Imag) from quadrature samples at step 94 (also elaborated below with respect to FIG. 10). From Vmag and Imag, the microcontroller 32 calculates impedance Z=Vmag/Imag and stores the calculated Z in a scan vector at step 95.

If it is determined at step 96 that the frequency sweep has been completed (max scan frequency attained), the scan is stopped at step 97 and the operating frequency is determined at step 98 as the minimum in the Z versus frequency curve (FIG. 8) minus the bias offset to place the operation on the linear portion of the slope of the impedance curve. The handpiece 20 frequency is then updated at step 99. On the other hand, if it is determined at step 96 that the frequency sweep has not been completed, the frequency is implemented by a fixed step size (e.g. 20 Hz) at step 100 and the handpiece 20 frequency is again updated at step 92. The process is then repeated until the scan is completed and the resonant frequency has been identified.

Figure 10:
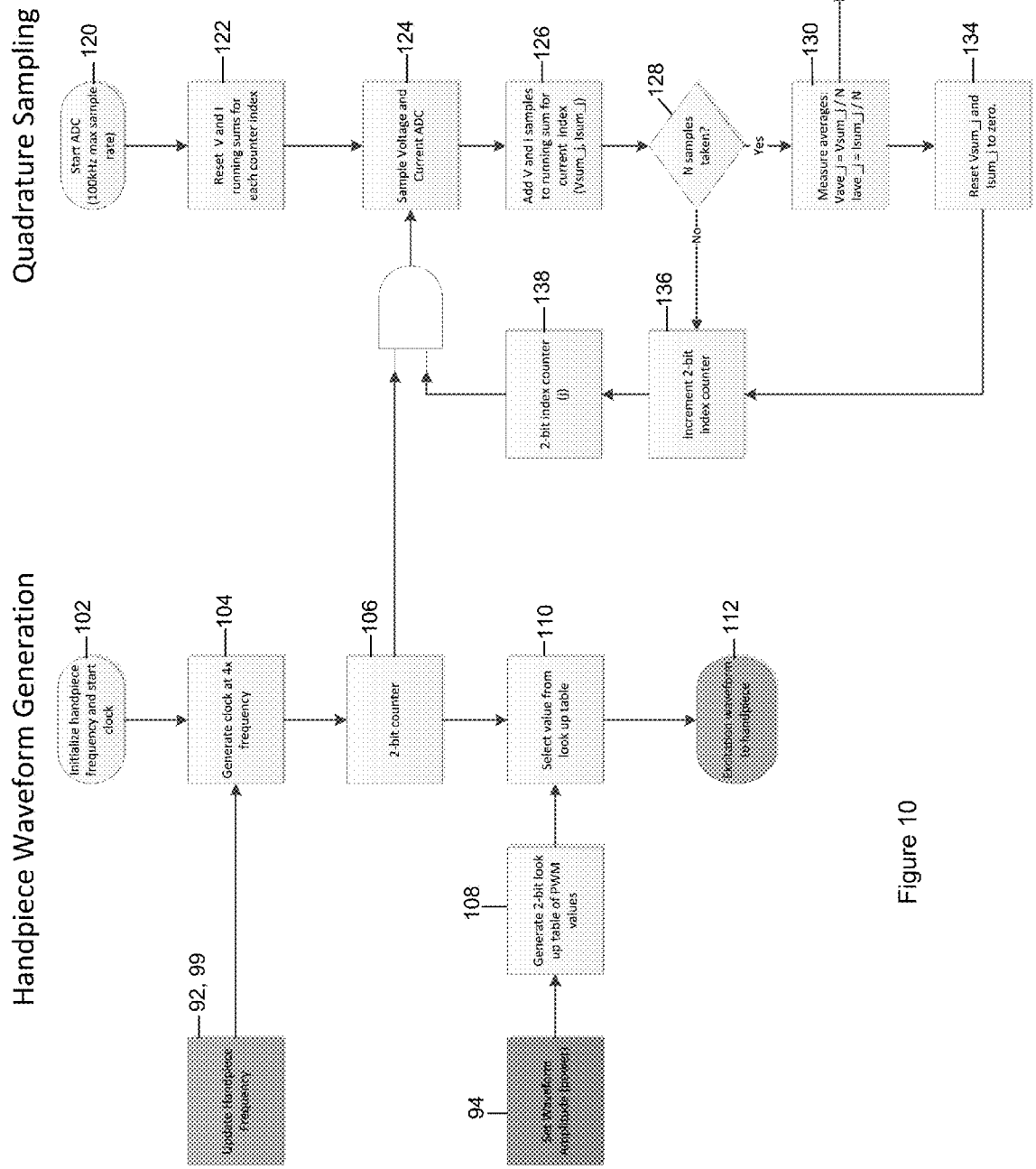
FIG. 10 illustrates an exemplary embodiment of the generation of the handpiece driving waveform and quadrature sampling for use in driving the ultrasonic handpiece as described with respect to FIG. 9.

FIG. 10 illustrates an exemplary embodiment of the generation of the handpiece driving waveform and quadrature sampling for use in driving the ultrasonic handpiece as described with respect to FIG. 9. As illustrated in FIG. 10, the handpiece 20 waveform generation or frequency update starts by initializing the handpiece frequency and starting the clock at step 102. Typically, the handpiece frequency starts at the resonant frequency of the ultrasonic transducer when no load is applied. The clock is generated at, for example, four times the desired output frequency at step 104. As appropriate, the clock frequency is updated based on an update request 92 or 99 as a result of the scan operation described with respect to FIG. 9. The clock frequency is then applied to the 2-bit counter 52 at step 106. As also illustrated, the Imag and Vmag values generated during the scan at step 94 may also be used to generate the 2-bit lookup table of PWM values at step 108 for readout during operation in order to provide an appropriate PWM signal of the type illustrated in FIG. 2 to create the desired sine wave signal. The output of the 2-bit counter at step 106 is then used to select a value from the lookup table at step 110 at the appropriate time. The values selected from the lookup table at step 110 are then used by the full bridge synchronous class D amplifier to generate an output to the resonant circuit 36 at step 112 as described above with respect to FIGS. 3-6.

As also shown in FIG. 10, the quadrature sampling (ADC) starts at step 120 using a set sample rate (e.g., 100 kHz max sample rate), and the V and I running sums for each counter index is reset at step 122. The voltage and current ADC is then sampled at step 124 using a logical AND of the output of the 2-bit counter and a feedback value of the 2-bit index counter (described below). The V and I samples are added into a running sum for the current index (Vsum_j, Isum_j) at step 126. It is then determined at step 128 if N samples have been taken and, if so, the voltage and current averages are calculated at step 130 as Vave_j=Vsum_j/N and Iave_j 32 Isum j/N. The stored values for Vave_j and Iave_j are updated at step 132. The Vsum_j and Isum_j values are then reset to zero at step 134. A 2-bit index counter is then incremented at step 136 to generate a 2-bit index counter value for the index j at 138 which is then logically ANDed with the 2-bit counter value to sample the voltage and current at step 126.

Those skilled in the art also will readily appreciate that many additional modifications and scenarios are possible in the exemplary embodiments without materially departing from the novel teachings and advantages of the invention. For example, the full wave synchronous class D amplifier of the drive circuit may be used with or without a feedback line so long as the proper adjustment signals are provided to the microcontroller. Accordingly, any such modifications are intended to be included within the scope of this invention as defined by the following exemplary claims.

What is claimed:

1. A magnetostrictive ultrasonic dental scaler, comprising:
a handpiece having an ultrasonic transducer that vibrates at an optimal operational frequency in response to an electromagnetic field applied thereto and an excitation coil that generates said electromagnetic field in response to an applied electrical signal;
a resonant circuit that generates said electrical signal; and
a control circuit comprising a microprocessor and a full bridge synchronous class D amplifier that generates a drive signal for said resonant circuit, said control circuit receiving sensed current and voltage outputs of said ultrasonic transducer as a result of changing impedance at said ultrasonic transducer, said microprocessor quadrature sampling said sensed current and voltage outputs at the same sampling rate as used for the generation of said electrical signal, generating a pulse width modulated signal from said quadrature sampled sensed current and voltage that represents a pulse train approximation of a sine wave of said drive signal, and said pulse train being applied to said full bridge synchronous class D amplifier to generate said drive signal, whereby changing pulse widths of the pulse train changes an amplitude of said drive signal.

2. A magnetostrictive ultrasonic dental scaler as in claim 1, wherein said resonant circuit comprises an LC resonant circuit that when coupled to the ultrasonic transducer produces a high Q resonant circuit in line with a physical resonance of the ultrasonic transducer.

3. A magnetostrictive ultrasonic dental scaler as in claim 1, further comprising an oscillator that generates a NCO frequency that is a multiple of an optimal operational frequency of said resonant circuit, said full bridge synchronous class D amplifier being driven at said NCO frequency.

4. A magnetostrictive ultrasonic dental scaler as in claim 3, wherein said NCO frequency is n times said optimal operational frequency whereby a cycle of said optimal operational frequency is divided into n samples each having a period of duration T1 corresponding to a 360°/n phase of said optimal operational frequency, said NCO frequency synchronizing a rate of the quadrature sampling with the optimal operational frequency of said ultrasonic transducer.

5. A magnetostrictive ultrasonic dental scaler as in claim 4, further comprising lookup tables that store respective values representing pulse durations of said pulse trains in each of the n periods of duration T1 for each side of said full bridge synchronous class D amplifier, wherein each lookup table stores respective pulses that are 180° out of phase with corresponding pulses sampled during the same sampling period of the other lookup table.

6. A magnetostrictive ultrasonic dental scaler as in claim 5, wherein corresponding pulses in the respective lookup tables are offset by a pulse width value that is adjustable so as to induce a bias current to enable dynamic adjustment of a bias current output by said resonant circuit.

7. A magnetostrictive ultrasonic dental scaler as in claim 5, further comprising an x bit counter, where $2^x=n$, that is clocked by said oscillator at said NCO frequency, a value of said x bit counter being used as an address for said lookup tables for each T1 period.

8. A magnetostrictive ultrasonic dental scaler as in claim 7, wherein said oscillator comprises a numerically controlled oscillator implemented within said microprocessor.

9. A magnetostrictive ultrasonic dental scaler as in claim 8, wherein said numerically controlled oscillator comprises an m-bit phase accumulator register that on each clock cycle of said NCO frequency is incremented by a frequency control word (FCW) whereby a current angular position of the numerically controlled oscillator is stored for a phase calculated as phase=$2*\pi*(FCW/2m)$.

10. A magnetostrictive ultrasonic dental scaler as in claim 9, wherein a most significant bit of the numerically controlled oscillator clocks said x bit counter.

11. A magnetostrictive ultrasonic dental scaler as in claim 8, wherein the optimal operational frequency of the ultrasonic transducer is determined by measuring an amplitude relationship between current and voltage outputs of said resonant circuit, wherein said amplitude relationship between current and voltage outputs of said resonant circuit are sampled as the same sampling rate as used at an output of said numerically controlled oscillator at specific values of said x-bit counter.

12. A magnetostrictive ultrasonic dental scaler as in claim 11, wherein voltage and current samples are taken 0, 90, 180, and 270 degrees phase shifted from the drive signal of the resonant circuit and said microprocessor calculates from the samples the amplitude relationship between current and voltage outputs of the resonant circuit as:

$$|V|=0.5*\text{sqrt}((V_0-V_{180})^2+(V_{90}-V_{270})^2)$$

$$|I|=0.5*\text{sqrt}((I_0-I_{180})^2+(I_{90}-I_{270})^2).$$

13. A magnetostrictive ultrasonic dental scaler as in claim 12, further comprising determining said impedance Z of said ultrasonic transducer as $Z=|V|/|I|$, where V is the output voltage of said resonant circuit and I is the input current of said ultrasonic transducer and said optimal operational frequency is a frequency at a central location on a downward slope of impedance Z versus frequency on a curve of impedance Z versus frequency.

14. A magnetostrictive ultrasonic dental scaler as in claim 1, wherein said microprocessor controls said resonant circuit to generate said electrical signal to excite said ultrasonic transducer at a variety of frequencies in a frequency range, calculates the impedance Z of said ultrasonic transducer at each of said variety of frequencies, and determines said optimal operational frequency as a frequency in said frequency range at which the impedance has a minimum value on an impedance versus frequency curve.

15. A magnetostrictive ultrasonic dental scaler as in claim 1, further comprising a Hall effect current sensor that senses an output current of said resonant circuit.

16. A magnetostrictive ultrasonic dental scaler as in claim 1, wherein said sensed current and voltage outputs of said ultrasonic transducer are provided via a feedback wire from a feedback loop including said excitation coil.

17. A magnetostrictive ultrasonic dental scaler as in claim 1, further comprising a display screen including a touch panel display that controls power applied to the ultrasonic transducer so as to change the output amplitude of the ultrasonic transducer in response to touch panel inputs to the touch panel display.

18. A magnetostrictive ultrasonic dental scaler as in claim 17, further comprising an asynchronous data line that transmits and receives data between the display and said microprocessor whereby when an event is changed on the display information relating to the change is transmitted on the asynchronous data line to the microprocessor, which interprets the display information and changes the power applied to the ultrasonic transducer and transmits update information back to the display to update a status of the display.

19. A magnetostrictive ultrasonic dental scaler as in claim 1, further comprising a potentiometer controlling power and individual switches controlling functions whereby changes to the potentiometer and/or individual switches provide a direct analog signal into the microprocessor and the microprocessor interprets any changes in the analog signal to accordingly control power applied to the ultrasonic transducer.

20. A magnetostrictive ultrasonic dental scaler as in claim 1, wherein the control circuit is responsive to a dental chair control panel including a potentiometer or a touch display that provide desired changes in the power applied to the ultrasonic transducer to said microprocessor which controls power applied to the ultrasonic transducer.

21. A method for controlling a magnetostrictive ultrasonic transducer, comprising:
generating a drive signal for a resonant circuit using a full bridge synchronous class D amplifier;
said resonant circuit outputting an electrical signal for driving an excitation coil that causes said magnetostrictive ultrasonic transducer to vibrate in response to an electromagnetic field generated by said excitation coil in response to said electrical signal applied thereto;
measuring current and voltage outputs of said ultrasonic transducer
by quadrature sampling said measured current and voltage outputs at the same sampling rate as used for the generation of said electrical signal by said resonant circuit;
generating a pulse width modulated signal from said quadrature sampled sensed current and voltage that represents a pulse train approximation of a sine wave of said drive signal; and
said pulse train being applied to said full bridge synchronous class D amplifier to generate said drive signal, whereby changing pulse widths of the pulse train changes an amplitude of said drive signal.

22. A method as in claim 21, wherein said quadrature sampling step includes an oscillator generating a NCO frequency that is a multiple of an optimal operational frequency of said resonant circuit and driving said full bridge synchronous class D amplifier at said NCO frequency.

23. A method as in claim 22, wherein said NCO frequency is n times said optimal operational frequency whereby a cycle of said optimal operational frequency is divided into n samples each having a period of duration T1 corresponding to a 360°/n phase of said optimal operational frequency, said NCO frequency synchronizing a rate of the quadrature sampling with the optimal operational frequency of said ultrasonic transducer.

24. A method as in claim 23, further comprising storing respective values representing pulse durations of said pulse trains in each of the n periods of duration Ti in lookup tables for each side of said full bridge synchronous class D amplifier, wherein each lookup table stores respective pulses that are 180° out of phase with corresponding pulses sampled during the same sampling period of the other lookup table.

25. A method as in claim 24, wherein corresponding pulses in the respective lookup tables are offset by a pulse width value that is adjustable so as to induce a bias current to enable dynamic adjustment of a bias current output by said resonant circuit.

26. A method as in claim 24, further comprising clocking an x bit counter at said NCO frequency, where $2^x=n$, and using a value of said x bit counter as an address for said lookup tables for each T1 period.

27. A method as in claim 26, further comprising generating said sampling frequency using a numerically controlled oscillator.

28. A method as in claim 27, further comprising implementing said numerically controlled oscillator as an m-bit phase accumulator register that on each clock cycle of said NCO frequency is incremented by a frequency control word (FCW) and storing a current angular position of the numerically controlled oscillator for a phase calculated as phase=$2*\pi*(FCW/2m)$.

29. A method as in claim 28, wherein said x bit counter is clocked by a most significant bit of the numerically controlled oscillator.

30. A method as in claim 27, wherein the optimal operational frequency of the ultrasonic transducer is determined by measuring an amplitude relationship between current and voltage outputs of said resonant circuit and sampling said amplitude relationship between current and voltage outputs of said resonant circuit at the same sampling rate as used at an output of said numerically controlled oscillator at specific values of said x-bit counter.

31. A method as in claim 30, further comprising taking voltage and current samples 0, 90, 180, and 270 degrees phase shifted from the drive signal of the resonant circuit and calculating from the samples the amplitude relationship between current and voltage outputs of the resonant circuit as:

$$|V|=0.5*\mathrm{sqrt}((V_0-V_{180})^2+(V_{90}-V_{270})^2)$$

$$|I|=0.5*\mathrm{sqrt}((I_0-I_{180})^2+(I_{90}-I_{270})^2).$$

32. A method as in claim 31, further comprising determining an impedance Z of said ultrasonic transducer as $Z=|V|/|I|$, where V is the output voltage of said resonant circuit and I is the input current of said ultrasonic transducer and said optimal operational frequency is a frequency at a central location on a downward slope of impedance Z versus frequency on a curve of impedance Z versus frequency.

33. A method as in claim 21, further comprising exciting said ultrasonic transducer at a variety of frequencies in a frequency range, calculating the impedance Z of said ultrasonic transducer at each of said variety of frequencies, and determining said optimal operational frequency as a frequency in said frequency range at which the impedance has a minimum value on an impedance versus frequency curve.

34. A method as in claim 21, further comprising providing said sensed current and voltage outputs of said ultrasonic transducer via a feedback wire from a feedback loop including said excitation coil.

* * * * *